United States Patent [19]

Hummel et al.

[11] Patent Number: 4,824,781

[45] Date of Patent: Apr. 25, 1989

[54] MICROBIOLOGICALLY PRODUCED D(-)-MANDELATE-DEHYDROGENASE PROCESS FOR OBTAINING IT AND ITS USE

[75] Inventors: Werner Hummel, Titz; Horst Schütte, Salzgitter; Maria-Regina Kula, Niederzier/Hambach; Wolfgang Leuchtenberger, Bruchköbel, all of Fed. Rep. of Germany

[73] Assignee: Degussa Aktiengesellschaft, Frankfurt am Main, Fed. Rep. of Germany

[21] Appl. No.: 917,440

[22] Filed: Oct. 10, 1986

[30] Foreign Application Priority Data

Oct. 15, 1985 [DE] Fed. Rep. of Germany ....... 3536662

[51] Int. Cl.$^4$ .......................... C12P 7/42; C12N 9/04; C12R 1/225
[52] U.S. Cl. ..................................... 435/146; 435/190; 435/853
[58] Field of Search ........................ 435/146, 136, 190

[56] References Cited

U.S. PATENT DOCUMENTS 4,609,623  9/1986  Leuchtenberger et al. ........ 435/130

FOREIGN PATENT DOCUMENTS 57-198096  12/1982  Japan ................................... 435/146

OTHER PUBLICATIONS

Bergly Manual of Systematic Bacteriology vol. 2 (1986), Sneath, et al., editors, Williams & Wilkins, Baltimore, pp. 1226 & 1228.

Primary Examiner—Thomas G. Wiseman
Assistant Examiner—Charles L. Patterson, Jr.
Attorney, Agent, or Firm—Cushman, Darby & Cushman

[57] ABSTRACT

The subject matter of the invention is a new D(−)-mandelate-dehydrogenase and obtaining it from Lactobacillus curvatus DSM 20019 (obtainable from the German Collection of Microorganisms). The new enzyme can be used for the enzymatic conversion of D(−)-mandelic acid and various other D-2-hydroxycarboxylic acids into the corresponding 2-ketocarboxylic acids or from benzoyl formate and various other 2-ketocarboxylic acids conversion to the corresponding D-2-hydroxycarboxylic acids.

10 Claims, No Drawings

MICROBIOLOGICALLY PRODUCED D(-)-MANDELATE-DEHYDROGENASE PROCESS FOR OBTAINING IT AND ITS USE

SUMMARY OF THE INVENTION

A subject matter of the invention is a previously non-described enzyme which catalyzes the following reaction:

$$R-\underset{O}{\overset{H}{C}}-COOH + NADH + H^+ \rightleftharpoons R-\underset{OH}{\overset{H}{C}}-COOH + NAD^+$$

D-Configuration

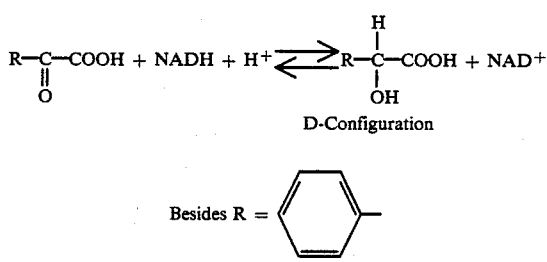

Besides R =

R can also be various straight or branched chain aliphatic and araliphatic groups, e.g., methyl, ethyl, propyl, butyl, isopropyl, isobutyl, methylmercaptoethyl, 1-methylpropyl, tert.butyl, phenylmethyl, benzyl, phenylethyl, 4-hydroxyphenylmethyl, 3,4-dihydroxyphenylmethyl.

Especially well accepted is the substrate benzoyl formate (phenyl glyoxylate) which is reduced with good activity stereospecifically to D(—)-mandelate. The hydrogen for the reduction reaction is supplied by the coenzyme NADH (nicotinamide-adenine-dinucleotide). The equilibrium of the reaction is on the side of the D(—)-mandelic acid, so that, especially in continuous carrying out of the reaction with steady regeneration of the coenzyme, benzoyl formate can be converted in high yields into D(—)-mandelic acid.

The microbiologically produced D(—)-mandelate-dehydrogenase produced according to the invention is characterized by the following physical-chemical properties.

(1) Reactivity

It reacts in the presence of NADH (nicotinamide-adenine-dinucleotide) with benzoyl formate with formation of D(—)-mandelate and in the presence of NAD+ with D(—)-mandelate with formation of benzoyl formate;

(2) Substrate Specificity

It reduces particularly well benzoyl formate, besides also other aliphatic or araliphatic 2-ketocarboxylic acids and oxidizes especially well (D—)-mandelate, besides also other aliphatic or araliphatic D-2-hydroxycarboxylic acids;

(3) Optimum pH

The opimum pH for the reduction reaction is 6.0+0.5, the optimum pH for the oxidation reaction is 8.5.

(4) pH-Stability

After storing for one week at 4° C. and a pH between 5 and 7.5, it shows a residual activity of >85%;

(5) Optimal Temperature

The optimal temperature is 55° C. at a pH of 6.0;

(6) Temperature Stability

Treated for 15 minutes at a pH of 6.0 at 50° C. the residual activity is 90%;

(7) Activity

It shows a specific activity of about 2100 U/mg protein;

(8) Influence of Inhibitors

It is strongly inhibited by $HgCl_2$, $CuSO_4$ or mercuri-p-chlorobenzoate;

(9) Molecular Weight

The molecular weight is 60,000±5000 (determined by gel filtration);

(10) Molecular Weight of the Subunit

The molecular weight of the subunit is 30,000±3000 (determined by SDS-electrophoresis);

(11) $K_M$ Value

The $K_M$ value for the reduction reaction for the substrate benzoyl formate at pH 7.0 is 0.22 mM, the $K_M$ value for the oxidation reaction for the substrate D(—)-mandelate at pH 8.0 is 0.5 mM.

The D(—)-mandelate-dehydrogenase of the invention can be obtained from *Lactobacillus curvatus* DSM 20019 (German Collection of Microorganisms 20019).

A further subject of the invention, therefore, is a process for obtaining the D(—)-mandelate-dehydrogenase which is characterized by anaerobically cultivating Lactobacillus curvatus DSM 20019 in an aqueous nutrient medium which contains a source of carbon and nitrogen, thiamine and mineral salts at a pH between 5.5 and 6.5 and a temperature between 30° and 37° C., separating off the cell mass and isolating the enzyme from the cells.

The last subject matter of the invention is the use of the D(—)-mandelate-dehydrogenase for the production of D(—)-mandelic acid (and other aliphatic and araliphatic acids) from benzoyl formate (and other aliphatic and araliphatic ketoacids).

To obtain the enzyme of the invention, there was first carried out a screening with 45 strains of the family Lactobacillaceae (Lactobacillus, Leucostonoc and Pediococcus). The strains for this screening were grown on a 300 ml scale under conditions which were recommended for each strain in the DSM catalogue, customarily in DSM medium No. 11 (MRS medium) at 30° or 37° C.

After 20 hours growth, the cell mass was harvested by centrifugation (20 minutes at 10,000 rpm), suspended in potassium phosphate buffer (0.1M; pH 7.5) (4 ml of buffer solution per 1 gram of wet bacteria mass) and then broken up in a laboratory shaker containing glass beads. The insoluble cell components and the glass beads were separated off by centrifugation (2 minutes at 12,000 rpm) and the supernatant (crude extract) was tested for its enzymatic activity. To detect the enzyme, there was used a photometric test. The test mixture in each case contained 1 ml potassium phosphate buffer (0.1M; pH 7.0), 20 μl NADH (0.2 mM final concentration) and 20 μl benzoyl formate (2 mM final concentration and limiting amounts on the crude extract 1 to 20 μg protein).

The change in the extinction of NADH at 340 nm was recorded. From the values obtained, there was substrated a zero value which would be obtained if the test was carried out in the absence of benzoyl formate. The enzyme activity is stated in International Units, whereby one unit (U) indicates the consumption of 1 μMol NADH per 1 minute.

It shows that seven of the microorganisms tested exhibited a clear NADH-dependent activity in the reduction of benzoyl formate to D(−)-mandelate. The enzyme activities of the crude extracts are summarized in Table 1.

TABLE 1

Screening of D(−)-Mandelate-Dehydrogenase

| Strain | DSM-No. | U/mg | U/l | Stereospecifity On C-2 |
|---|---|---|---|---|
| Lactobacillus curvatus | 20 019 | 0.17 | 75 | D |
| L. delbrueckii | 20 074 | 0.08 | 43 | D |
| L. bulgaricus | 20 080 | 0.17 | 68 | D |
| L. casei | 20 178 | 0.13 | 55 | D |
| L. brevis | 20 054 | 0.08 | 58 | D |
| L. fructivorans | 20 203 | 0.12 | 65 | D |
| L. parvus | 20 177 | 0.11 | 55 | D |

To determine the stereospecificity of the enzyme, there was tested with the crude extracts the oxidation of D(−)- or L(+)-mandelate in the presence of NAD+ with the following test mixture:

1 ml Potassium phosphate buffer (0.1M; pH 8.0), 20 μl NAD+ (2.5 mM in the Test), 20 μl D(−)- or L(+)-Mandelic acid (9.5 mM in the Test) and limiting amounts of crude extract (5 to 50 μg Protein) in the Test.

The strain Lactobacillus curvatus DSM 20019 in the screening showed the highest activity and, therefore, was chosen for obtaining the enzyme of the invention.

To obtain the D(−)-mandelate-dehydrogenase of the invention Lactobacillus curvatus DSM 20019 was grown in the following medium:

| Glucose | 20 g |
|---|---|
| Yeast extract | 5 g |
| Universal peptone | 10 g |
| Meat extract | 5 g |
| Diammonium hydrogen citrate | 2 g |
| Sodium acetate | 5 g |
| Magnesium sulfate | 0.1 g |
| Manganese sulfate | 0.05 g |
| Dipotassium hydrogen phosphate | 2 g |
| Distilled water | 1 l. |

The pH of this solution was adjusted to 6.5, then the solution was sterilized for 15 minutes at 121° C. (2 bar). The microorganism was cultivated anaerobically; for this purpose it was sufficient if the medium was covered with nitrogen. After reaching a temperature of 30° C., the medium was innoculated with 300 ml of a 24 hour old preculture for a 10 liter scale. The activity of the D(−)-mandelate dehydrogenase reached its maximum value only during a short space of time, with prolonged growth, the activity falls off again.

On a 5000 liter scale, there can be used a 10 liter inoculum fermenter. From the 5000 liter fermenter, there is then obtained about 25 kg of wet bacterial mass. The pH, which drops during the course of the growth, is held in the fermenter at 5.5 with concentrated ammonia. The biomass can be intermittently stored for several months at −20° C. without large loss of activity.

The D(−)-mandelate-dehydrogenase of the invention can be recovered in the form of a crude extract through a disintegration of the cells according to customary methods, e.g., ultrasonic treatment or wet grinding, and separation of the insoluble cell fragments. The cell fragments, for example, in a 10 kg mixture are separated off through a first liquid-liquid extraction step into an aqueous two phase made of 10% (w/w) polyethylene glycol (Mol. Wt. 6000), 8% (w/w) phosphate buffer for pH 8.0 and 5000 ml of crude extract. The upper phase then contains the main amount of the D(−)-mandelate-dehydrogenase.

The upper phase is then subjected to a second liquid-liquid extraction step. For this purpose, the enzyme containing upper phase (3890 ml) is treated with 8% (wv) phosphate buffer for pH 6.1 and 0.3M sodium chloride, calculated on a final volume of 7,780 ml and stirred for 1 hour. The D-(−)-mandelate-dehydrogenase is now found in the lower phase of the polyethylene glycol-salt system formed.

For further purification, this lower phase salt solution can be diafiltered and subjected to DEAE-ion exchange-chromatography.

The process can comprise, consist essentially of, or consist of the stated steps with the recited material.

The invention will be explained in more detail through the following examples.

DETAILED DESCRIPTION

Example 1

Cultivation of the Microorganism

Lactobacillus curvatus DSM 20019 was grown in 10 liters of the medium already mentioned above. The pH of this medium was adjusted to 6.5, then the medium was sterilized for 15 minutes at 121° C. (2 bar). The medium was covered with nitrogen, cooled to a temperature of 30° C. and innoculated with 300 ml of a 24 hour old culture. The progress of enzyme activity in relation to the time of growth was tested by withdrawing samples at various times and after disintegration of the cells the activity of the D-(−)-mandelate-dehydrogenase in the crude extract was determined. The activity of the enzyme after about 15 hours growth reached a maximum and clearly fell off again upon a longer growth period. After 20 hours growth, there were obtained by centrifugation (20 minutes at 10,000 rpm) 50 grams of wet bacterial mass.

Example 2

Isolation and Purification of the Enzyme 2000 grams of wet bacterial mass from a 5000 liter cultivation are suspended, in 100 mM phosphate buffer for pH 7.5 with addition of 0.1 volume percent of 2-mercaptoethanol to reach a 40 weight percent cell suspension with a final volume of 5000 ml. The pH of the suspension was tested and adjusted with dilute potassium hydroxide. The cell content was released from the suspension cooled to 4° C. with the help of a glass bead mill (manufacturer: Bachofen; Dyno-Mill Type KDL). For this purpose, the 600 ml capacity grinding container was filled with glass beads of a diameter of 0.25 to 0.5 mm to a bulk volume of 510 ml. The cell disintegration was carried out operating the stirrer at 3000 rpm and a flow rate of 5 l/h. The cooling jacket and the stirrer shaft bear housing were cooled during the process with an ethylene glycol solution of −20° C. in order to avoid substantial warming of the suspension. After three passages, there was reached a degree of disintegration of over 90%. The pH of the suspension was adjusted to 7.0 with dilute aqueous potassium hydroxide.

There was produced an aqueous two-phase system which contained 10% (w/w) of polyethylene glycol (Mol. Wt. 6000), 8% (w/w) of phosphate buffer for pH 8.0 and 5,000 ml of the homogenized suspension in a total system of 10 kg. To establish the distribution equilibrium, the two-phase system was stirred for one hour, then it was separated by centrifugation. The upper phase (3890 ml) contained over 90% of the total D(−)-mandelate dehydrogenase present. The lower phase contained the fragments and foreign proteins extracted under these conditions and was discarded.

The upper phase was then treated with 8% (w/v) phosphate buffer for pH 6.1 and 0.3M sodium chloride, calculated on a final volume of 7.780 ml, and stirred for one hour. The polyethylene glycol/salt system formed completely separated in a settling vessel in about 1 hour. The salt rich lower phase (3620 ml) contained about 86% of the total D(−)-mandelate-dehydrogenase present.

The separated lower phase was concentrated with a hollow fiber system (Manufacturer: Amicon; PM 10, 1.8 ft$^2$) and diafiltered by addition of 5 mM potassium phosphate for pH 6.5 to a final concentration of 5 mM.

The concentrated and diafiltered enzyme solution was pumped to a column (5 cm × 14 cm) packed with DEAE-Sephacell. The ion exchanger was previously equilibrated against a buffer which contained 5 mM of potassium phosphate buffer for pH 6.5 and 0.1 volume percent of 2-mercaptoethanol. The column was subsequently washed with starting buffer, then the enzyme was eluted with a linear gradient (2 × 800 ml) of 0 to 0.5M sodium chloride in the starting buffer. The D(−)-mandelate-dehydrogenase was eluted with about 0.1M sodium chloride. The active fractions were concentrated by ultrafiltration, treated with 50 volume percent glycerol and stored at −20° C. The result of the purification step are summarized in Table 2. The purified enzyme had a specific activity of about 2100 U/mg of protein.

TABLE 2

| | Purification of the D(−)-Mandelate-Dehydrogenase | | | | | |
|---|---|---|---|---|---|---|
| Purification Step | Volume ml | Protein mg | Total activity U | Spec. Activity U/mg | Yield % | Enrichment -fold |
| Crude extract | 5 000 | 115 000 | 340 000 | 2.96 | 100 | 1 |
| Upper phase I | 3 890 | 4 079 | 323 000 | 79.2 | 95 | 26.8 |
| Lower phase II | 3 620 | 3 475 | 312 400 | 89.9 | 91.9 | 30.4 |
| Diafiltration | 540 | 2 821 | 275 000 | 97.5 | 80.9 | 32.9 |
| DEAE-Cellulose | 455 | 112 | 237 700 | 2122.0 | 70.0 | 717.0 |

Test with Benzoyl formate Purification from 2 000 g *Lactobacillus curvatus*-wet mass
Enzyme test:
2 850 μl  0.1 M Phosphate buffer for pH 6.0
  50 μl  14 mM NADH-Solution
 100 μl  30 mM Benzoyl formate-Solution
3 000 μl
Start of the Reaction with Enzyme Example 3

Relation of the Speed of Reaction of the Enzymatically Catalyzed Reaction to pH

The speed of the reaction of the reduction of benzoyl formate to D(−)-mandelate in presence of the D(−)-mandelate-dehydrogenase was investigated in relation to the pH of the reaction solution. The test mixture (3.00 ml) had the following composition: 0.25 mM NADH; 1.5 mM benzoyl formate, limiting amounts of enzyme, 0.1M of buffer of different composition and different pH values. The enzyme had a pH optimum between pH 5.5 and pH 6.5. The pH value was measured in the reaction mixture.

The speed of reaction of the dehydrogenation of D(−)-mandelate to benzoyl formate, catalyzed by the D(−)-mandelate-dehydrogenase was likewise investigated as to its relation to pH. The test mixture (3.00 ml) had the following composition: 4.5 mM NAD+, 2 mM D(−)-mandelate, limiting amounts of enzyme, 0.1M of buffer of different composition. The dehydrogenation reaction showed an optimum at pH 8.5.

Example 4

Storage Stability of the D(−)-Mandelate-Dehydrogenase in Relation to pH

D(−)-mandelate-dehydrogenase was incubated in 0.1M buffer of different composition at a protein concentration of 5 mg/ml for one week at 4° C. Then the residual activity was determined as described in Example 3 using 0.1M phosphate buffer for pH 6. Thereby, it showed a good pH stability in the range of pH 5 to 7.5. After one week, there was still detectable 85% of the activity, in phosphate buffer at 6.5, even 98%.

Example 5

Temperature Stability of the D(−)-Mandelate-Dehydrogenase

Purified D(−)-mandelate-dehydrogenase (DEAE-Sephacell Peak 2122 U/mg) was incubated at various temperatures in the presence of 0.1M phosphate buffer for pH 6.0 which contained 5 mg/ml of bovine serum albumen and at specific times the residual activity ascertained. At a temperature of 50° C., the residual activity after 15 minutes was still about 90%. At higher temperatures, the enzyme was quickly inactivated.

Example 6

Influence of the Temperature on the Enzyme Activity

The speed of reaction of the reduction of benzoyl formate to D(−)-mandelate was measured in relation to the reaction temperature. The maximum speed of reaction was reached at 55° C. At the standard measuring temperature of 30° C. the speed of reaction was about 85% of the maximum value. Above 55° C. the speed of reaction dropped sharply because of the simultaneous denaturation of the enzyme.

Example 7

Determination of the Molecular Weight of the D(−)-Mandelate-Dehydrogenase and Determination of the Subunits The molecular weight of the native enzyme was ascertained by gel filtration on Superose 12. The column (1.0 cm×30 cm) coupled to a FPLC-system was operated with a flow rate of 0.4 ml/minute, whereby as test material there served 100 μl of the enzyme purified on DEAE-Sephacell. As standard proteins there were used cytochrome C, pepsin, egg albumin, bovine serum albumin (BSA); D-2-hydroxyisocaproate-dehydrogenase, L-2-hydroxyisocaproate-dehydrogenase, aldolase, L-alanine-dehydrogenase and L-leucine-dehydrogenase both from Bacillus cereus and ferritin. The molecular weight of the D(−)-mandelate was 60,000±5000 Dalton. Through gel electrophoresis in the presence of sodium dodecyl sulfate (SDS), the size and number of subunits of the enzyme could be determined. The molecular weight of the subunit was 30,000±3,000 Dalton. The D(−)-mandelate-dehydrogenase accordingly consisted of two subunits identical in size. For the standard curve there were used hemoglobin, β-lactoglobulin, chymotrypsinogen, pepsin, egg albumin, and BSA.

Example 8

Influence of Various Reagents and Metal Ions on the Enzymatic Activity of the D(−)-Mandelate-Dehydrogenase The speed of reaction of the reduction of benzoyl formate to D(−)-mandelate was measured in the presence of various reagents and metal ions. The enzyme was incubated for this purpose first for 5 minutes at 20° C. with the respective inhibitor or metal salt and then the remaining volume activity determined under normal conditions. The D(−)-mandelate-dehydrogenase was strongly inhibited in the presence of 0.1 mM $HgCl_2$, $CuSO_4$ or mercuric-p-chlorobenzoate while the presence of the other reagents, even at 1 mM had no great influence. The complete results are shown in Table 3.

TABLE 3

Inhibition of the D(−)-Mandelate-Dehydrogenase (− = Not Tested)

| Reagent | Relative Activity (%) | | |
|---|---|---|---|
| | 0.1 mM | 1 mM | 10 mM |
| Without Additive | 100 | 100 | 100 |
| $MgCl_2$ | 99 | 89 | 81 |
| $CaCl_2$ | 95 | 90 | — |
| $CuSO_4$ | 6.4 | 6.1 | — |
| $CoSO_4$ | 97 | 91 | — |
| $CdCl_2$ | 93 | 82 | — |
| $K_2Cr_2O_7$ | 99 | — | — |
| $FeCl_3$ | 91 | — | — |
| $ZnCl_2$ | 94 | 88 | — |
| $NiCl_2$ | 95 | 91 | 68 |
| $Na_2MoO_4$ | 90 | 88 | 73 |
| $HgCl_2$ | 0 | 0 | 0 |
| EDTA | 94 | 93 | 87 |
| 1.10 Phenanthroline | 96 | 96 | — |
| 2.2-Dipyridil | 100 | 99 | 86 |
| Iodacetamide | 98 | 96 | 91 |
| KCN | 84 | 81 | 71 |
| Mercuri-p-chlorobenzoate | 6 | — | — |
| 2-Mercaptoethanol | 96 | 93 | 90 |
| Dithiothreitol | 100 | 100 | 100 |

Example 9

Dependency of the Speed of Reaction On the Substrate Concentrations

The relation of the speed of reaction for the reduction of benzoyl formate to D(−)-mandelate to the concentration of the coenzyme NADH was investigated in the following test mixtures:

0.1M phosphate buffer for pH 7.0; 6 mM of benzoyl formate, limiting amounts of enzyme (enriched preparation, according to DEAE-cellulose-chromatography see Table 2); the NADH-concentration in the test mixtures was varied in the range of 0.01 to 0.30 mM. It showed that the optimum speed of reaction was reached at 0.25 mM. The $K_M$-value was 0.036 mM.

The reduction of benzoyl formate to D(−)-mandelate in relation to the benzoyl formate concentration was investigated in the following test mixture:

0.1M phosphate buffer for pH 7.0, 0.25 mM NADH and limiting amounts of enzyme. The benzoyl formate concentration was varied in the range of 0.02 mM to 8 mM. It showed that the optimum speed of reaction was reached at 1.5 mM. The $K_M$ value was 0.22 mM.

The reduction of various 2-keto-carboxylic acid in relation to the ketocarboxylic acid concentration was investigated. For the purpose there was used the following test mixture.

0.1M phosphate buffer for pH 7.0, 0.25 mM NADH with limiting amounts of enzyme (enriched preparation, after DEAE-cellulose chromatography, see Table 2). The 2-ketoacid concentration was varied in each case within the range of 0.05 to 9 mM and the decrease of the extinction through the NADH consumed in the reaction measured at 340 nm. The initial speed of reaction was evaluated according to the Michaelis-Menten equation. The found kinetic constants $V_{max}$ and $K_M$ are summarized in Table 4.

TABLE 4

Substrate Specifity of the D(−)-Mandelate-Dehydrogenase

| Substrate | Max. Initial Reaction Speed $V_{max}$ (%) (relative to Benzoyl formate) | $K_M$ Value (M) |
|---|---|---|
| 2-Ketobutyrate | 51 | $5.5 \times 10^{-4}$ |
| 2-Ketovalerate | 76 | $1.7 \times 10^{-4}$ |
| 2-Ketocaproate | 74 | $1.0 \times 10^{-4}$ |
| 2-Ketooctanoate | 6 | $3.5 \times 10^{-4}$ |
| 2-Keto-3-methylbutyrate | 176 | $1.8 \times 10^{-4}$ |
| 2-Keto-3 methylvalerate | 119 | $9.5 \times 10^{-5}$ |
| 2-Ketoisocaproate | 76 | $9.0 \times 10^{-5}$ |
| 2-Keto-4-methylmercapto-butyrate | 68 | $1.1 \times 10^{-4}$ |
| Trimethylpyruvate | 15 | $5.4 \times 10^{-3}$ |
| Benzoylformate | 100 | $2.2 \times 10^{-4}$ |
| Phenylpyruvate | 63 | $1.5 \times 10^{-4}$ |
| 4-Hydroxyphenylpyruvate | 4 | $6.5 \times 10^{-4}$ |
| 3-(3′-4′) Dihydroxyphenyl-pyruvate | 4 | $3.7 \times 10^{-4}$ |

The relation of the speed of reaction for the dehydrogenation of the D(−)-mandelate to the NAD+ concentration was investigated in the following test mixture:

0.1M Tris/HCl-buffer for pH 8.5, 2 mM D-(−)-mandelate, limiting amounts of enzyme. The NAD+ concentration was varied in the range of 0.05 mM to 6 mM and the increase of the extinction through the NADH formed in the reaction measured at 340 nm. It showed that the optimum reaction was reached at a concentration of 3 mM. The $K_M$ value for NAD+ was 0.20 mM.

The relation of the speed of reaction of the dehydrogenation of D-2-hydroxycarboxylic acids to the concentration of different D-2-hydroxycarboxylic acids was investigated in the following test mixture:

0.1-M phosphate buffer for pH 8.0, 3 mM NAD+ and limiting amounts of enzyme. The concentration of the 2-hydroxyacids was varied in the range from 0.25 to 300 mM. If no chiral D-2-hydroxyacid are available, there was employed the racemate. The extinction of the NADH formed in the reaction was measured at 340 nm. The initial speed of reaction was evaluated according to Michaelis-Menten and the kinetic constants $V_{max}$ and $K_M$ ascertained. The found kinetic constants are summerized in Table 5.

The relation of the speed of reaction of the dehydrogenation of D(—)-mandelate to the concentration of the D(—)-mandelate was investigated in the following test mixture:

0.1M phosphate buffer for pH 8.0, 3 mM NAD+ and limiting amounts of enzyme. The concentration of the D(—)-mandelate was varied in the range from 0.1 to 20 mM.

The extinction of the NADH formed in the reaction was measured at 340 nm. It showed that the optimum conversion was reached at a concentration of 6 mM.

The $K_M$ value for D(—)-mandelate was 0.5 mM.

TABLE 5

Substrate Specifity of the
D(—)-Mandelate-Dehydrogenase

| Substrate | max. Initial Reaction Velocity $V_{max}$ (%) (relative to D(—)-Mandelate | $K_M$-Value$^a$ (M) |
|---|---|---|
| D,L-2-Hydroxyvalerate | 128 | $1.3 \times 10^{-2}$ |
| D,L-2-Hydroxycaproate | 67 | $1.8 \times 10^{-3}$ |
| D,L-2-Hydroxyoctanoate | 3 | $2.2 \times 10^{-3}$ |
| D,L-2-Hydroxyisocaproate | 132 | $1.1 \times 10^{-3}$ |
| D-2-Hydroxy-4-methylmercapto-butyrate | 118 | $3.8 \times 10^{-3}$ |
| D,L-2-Hydroxy-4-methylmercapto-butyrate | 142 | $1.1 \times 10^{-3}$ |
| D,L-Phenyllactate | 22 | $2.5 \times 10^{-3}$ |
| D-Mandelate | 100 | $5 \times 10^{-4}$ |
| D,L-Mandelate | 100 | $4 \times 10^{-4}$ |
| L-Mandelate | 0 | — |

$^a$For the concentration of the D-enantiomer in the D,L-compounds there was assumed 50%.

Example 10

Continuous Production of D(—)-Mandelic Acid

A synthesis of chiral hydroxyacids in continuous operation is possible in an enzyme membrane reactor using molecular weight enlarged NADH bound to polyethylene glycol. The PEG-NADH was produced according to German Pat. No. 3,841,414. The modified coenzyme and the formate-dehydrogenase enzyme employed (for the coenzyme regeneration) and D(—)-mandelate-dehydrogenase were held back to the reaction by an ultrafiltration membrane YM 5 (CECl, Amicon Company), while the lower molecular weight compounds of the reaction solution (unreacted substrates, products, buffer) were removed (residence time 2 hours). The volume of the reactor was held constant by dosing in the same amount from a reservoir of 50 mM of benzoyl formate in buffer (0.3M Na-formate, 0.1M Tris-HCl pH 7.0) as the ultrafiltrate left the reactor.

The reactor volume was 10 ml; it contained in detail:
300 mM sodium formate solution (pH 7.0)
100 mM Tris-HCl (pH 7.0)
0.2 mM PEG$_{20000}$-NADH
2 U/ml formate-dehydrogenase (prepared according to Kroner et al (1982) *J. Chem. Technol. Biotechnol.*, Vol. 32, pages 130-137).
2 U/ml mandelate-dehydrogenase (prepared according to DEAE-cellulose-chromatography; see Table 2).
50 mM benzoyl formate.

The degree of reaction was determined, by the rotary value a. The product solution was measured polarimetrically (Polarimeter 241, Perkin-Elmer Co.; measured at 436 nm (Hg) at 27° C.). The concentration of product can then be acertained from a standard curve which was prepared with commercial D(—)-mandelate (Sigma M 2500).

Table 6 shows that conversions up to practically 100% can be reached.

TABLE 6

Continuous Reaction of Benzoyl Formate to
D-(—)-Mandelate

| Reaction Time [Hours] | Rotary Value [Degree] | Product Concentration [mM] | Conversion [%] |
|---|---|---|---|
| 2 | −0.98 | 25 | 51 |
| 5 | −1.85 | 48 | 96 |
| 10 | −1.92 | 50 | 100 |
| 20 | −1.92 | 50 | 100 |
| 30 | −1.92 | 50 | 100 |
| 40 | −1.92 | 50 | 100 |
| 50 | −1.92 | 50 | 100 |
| 60 | −1.92 | 50 | 100 |
| 70 | −1.92 | 50 | 100 |
| 80 | −1.92 | 50 | 100 |

The entire disclosure of German priority application No. P3536662.1 is hereby incorporated by reference.

What is claimed is:

1. A purified form of a microbiologically produced D(—)-mandelate-dehydrogenase having the following physical-chemical properties:
  (i) reactivity:
  said dehydrogenase reacts in the presence of NADH (nicotinamide-adenine-dinucleotide) with benzoyl formate to form D(—)-mandelate and in the presence of NAD+ with D(—)-mandelate to form benzoyl formate;
  (ii) substrate specificity:
  said dehydrogenase reduces aliphatic and araliphatic 2-ketocarboxylic acids and oxidizes aliphatic and araliphatic D-2-hydroxycarboxylic acids;
  (iii) optimum temperature and pH:
  at a temperature of 55° C. the optimum pH for said reduction reaction of (ii) above is 6.0±0.5 and the optimum pH for said oxidation reaction of (ii) above is 8.5;
  (iv) pH stability:
  after storage for one week at 4° C. at a pH between 5 and 7.5, said dehydrogenase has a residual activity of at least 85%;
  (v) temperature stability:
  said dehydrogenase treated for 15 minutes at a pH of 6.0 at 50° C. has a residual activity of 90%;
  (vi) activity:
  said dehydrogenase has a specific activity of about 2100 U/mg protein;

(vii) influence of inhibitors:
said dehydrogenase is strongly inhibited by $HgCl_2$, $CuSO_4$ and mercuri-p-chlorobenzoate;
(viii) molecular weight:
said dehydrogenase has a molecular weight of $60,000 \pm 5,000$ (determined by gel filtration);
(ix) molecular weight of a subunit of said dehydrogenase:
the molecular weight of said subunit is $30,000 +/- 3,000$ (determined by SDS-electrophoresis);
(x) $K_M$ value:
the $K_M$ value for said reduction reaction of (ii) above when said substrate is benzoyl formate, at pH 7.0, is 0.22 mM, the $K_M$ value for said oxidation reaction of (ii) above when said substrate is D(−)-mandelate, at pH 8.0, is 0.5 mM.

2. A process for obtaining the D(−)-mandelate-dehydrogenase according to claim 1 comprising:
(i) anaerobically cultivating *Lactobacillus curvatus* DSM 20019 in an aqueous nutrient medium which contains a source of carbon and nitrogen, thiamine and mineral salts at a pH between 5.5 and 6.5 and a temperature between 30° and 37° C.,
(ii) separating off a cell mass from said medium, and
(iii) isolating said dehydrogenase from said cell mass.

3. A process for the production of an aliphatic or araliphatic D-2-hydroxycarboxylic acid from a corresponding 2-ketocarboxylic acid comprising reacting said ketocarboxylic acid with said D(−)-mandelate-dehydrogenase according to claim 1 in the presence of NADH.

4. A process according to claim 3 wherein said ketocarboxylic acid is selected from the group consisting of benzoyl formate, 2-ketobutyrate, 2-ketovalerate, 2-ketocaproate, 2-ketooctanoate, 2-keto-3-methylbutyrate, 2-keto-3-methylvalerate, 2-ketoisocaproate, 2-keto-4-methylmercapto-butyrate, trimethylpyruvate, phenylpyruvate, 4-hydroxyphenylpyruvate and 3-(3',4') dihydroxyphenylpyruvate.

5. A process according to claim 4 wherein said ketocarboxylic acid is benzoyl formate and D(−)-mandelic acid is produced.

6. A process according to claim 5 wherein the pH is $6.0 \pm 0.5$.

7. A process for the production of an aliphatic or araliphatic 2-ketocarboxylic acid from a corresponding D-2-hydroxycarboxylic acid comprising reacting said D-2-hydroxycarboxylic acid with said D(−)-mandelate-dehydrogenase according to claim 1 in the presence of NAD+.

8. A process according to claim 7 wherein said hydroxycarboxylic acid is selected from the group consisting of the D or D,L form of 2-hydroxyvaleric acid, 2-hydroxycaproic acid, 2-hydroxyoctanoic acid, 2-hydroxisocaproic acid, 2-hydroxy-4-methylmercaptobutyric acid, 2-hydroxy-4-methylmercaptobutyric acid, phenyllactic acid and mandelic acid.

9. A process according to claim 8 wherein said hydrocarboxylic acid is selected from the group consisting of D-mandelic acid and D,L-mandelic acid and benzoyl formate is produced.

10. A process according to claim 8 wherein the pH is 8.5.

* * * * *